(12) United States Patent
Weber et al.

(10) Patent No.: US 6,781,774 B2
(45) Date of Patent: Aug. 24, 2004

(54) TUBE ASSEMBLY FOR AN OPTICAL INSTRUMENT HAVING AT LEAST TWO ROTARY JOINTS

(75) Inventors: Lauric Weber, Aalen (DE); Wolfgang Robra, Bad Wildbach (DE); Werner Koch, Keltern (DE)

(73) Assignee: Carl-Zeiss-Stiftung, Heidenheim (DE)

( * ) Notice: Subject to any disclaimer, the term of this patent is extended or adjusted under 35 U.S.C. 154(b) by 0 days.

(21) Appl. No.: 10/237,105

(22) Filed: Sep. 9, 2002

(65) Prior Publication Data

US 2003/0117727 A1 Jun. 26, 2003

(30) Foreign Application Priority Data

Sep. 7, 2001 (DE) .......................... 101 44 033

(51) Int. Cl.[7] .............................................. G02B 7/18
(52) U.S. Cl. ........................................ 359/831; 359/384
(58) Field of Search .................. 359/368, 379, 359/382, 384, 431, 831, 819, 822

(56) References Cited

U.S. PATENT DOCUMENTS 3,638,973 A 2/1972 Poletti
4,270,845 A 6/1981 Takizawa et al.
4,605,287 A 8/1986 Lang et al.
5,564,667 A 10/1996 Copeland et al.

FOREIGN PATENT DOCUMENTS

| DE | 27 13 737 | 10/1978 |
| EP | 1 120 676 | 8/2001 |
| JP | 2000-139949 | 11/1998 |

*Primary Examiner*—Euncha P. Cherry
(74) *Attorney, Agent, or Firm*—Walter Ottesen

(57) ABSTRACT

The invention relates to a tube for an optical instrument, such as a microscope, having several rotary joints (19, 20, 21) connected serially one behind the other. Each of the rotary joints (19, 20, 21) includes a brake (32, 33, 38) via which the rotary joints are secured against an unintended rotation. The brakes of the rotary joints (19, 20, 21), which are connected serially one behind the other, are simultaneously releasable by actuation of the single operator lever (39). For this purpose, a system of pins (42) and tilt levers (43) is mounted in the tube via which the actuation of the operator element (39) is transmitted to the brakes (32, 33, 38) connected serially one behind the other.

18 Claims, 3 Drawing Sheets

TUBE ASSEMBLY FOR AN OPTICAL INSTRUMENT HAVING AT LEAST TWO ROTARY JOINTS

FIELD OF THE INVENTION

The invention relates to a tube assembly for an optical instrument, such as a microscope, having at least two rotary joints.

BACKGROUND OF THE INVENTION

From U.S. Pat. No. 4,605,287, a surgical microscope for two operators is known which includes a viewing tube for the surgeon and a second viewing tube for the assistant. The viewing tube for the assistant includes a rotary joint location, which lies perpendicular to the tube axis and about which the ocular view can be rotated by 360° relative to the base part of the assistant viewing tube with which the assistant viewing tube is accommodated on the surgical microscope. Furthermore, the assistant viewing tube includes a further rotary joint position about which the assistant viewing tube can be rotated about the optical axis of the main viewing tube.

The rotational joints of the assistant viewing tube function so that the assistant can bring, relative to the main body of the surgical microscope, his ocular view into a position ergonomically favorable for him. Mutually conflicting requirements are present with respect to the friction forces in the rotary joints. On the one hand, the friction forces should be so high that the rotary joints stay in an adjusted position and are not pivoted into another position unintentionally because of small forces; on the other hand, in those cases, in which a changed rotation of the tube parts relative to each other is wanted, the rotation should be possible with forces as small as possible and, if possible, with one hand.

SUMMARY OF THE INVENTION

It is an object of the invention to provide a tube assembly which accommodates the above mutually opposing requirements.

The tube assembly of the invention is for an optical instrument and includes: a first rotary joint; a first brake for latching the first rotary joint; a second rotary joint; a second brake for latching the second rotary joint; an operator-controlled device operatively connected to the first and second brakes; and, the operator-controlled device being switchable between a first state wherein the first and second brakes are applied to the rotary joints and a second state wherein the first and second brakes are released to permit movement of the rotary joints.

The tube assembly of the invention includes at least two rotary joints. The rotary joints are latchable by means of brakes. A common operator lever is provided for releasing the brakes. When the operator lever is actuated, both rotary joints are enabled and, in the case of more than two rotary joints, all rotary joints are enabled.

When the operator lever is not actuated, the rotary joints are latched by the brakes. An unintended rotation of the rotary joints is thereby precluded. If, in contrast, a rotation is wanted, then the user can release the brakes. The rotary joints are no longer held when the brakes are released. For this reason, the rotation can take place with the slightest application of force. Because all brakes are released simultaneously with an actuation of the operator lever, the operating advantage results that the user must not think in advance about which rotary joint position a rotation has to take place in order to bring the ocular viewing location into the wanted position. Instead, the operator simply has to actuate the single operating lever and, thereupon, pivot the ocular viewing location into the wanted new position and then latch the brakes in this new position by releasing the operator lever.

The operator lever for the brakes is preferably mounted on the tube at the ocular end or user end.

There are various possibilities for the transmission of the movement of the operator lever. For example, an electrical transmission can be provided and, in this case, the brakes would have to be electromagnetically configured. If there is no power supply at or in the tube, the transmission of the movement of the operator lever can also take place strictly mechanically via pins and deflecting levers. The brakes themselves can then be configured to be strictly mechanical.

In a preferred embodiment of a mechanical transmission of the movement of the operator lever to the brakes, the brakes are releasable via an application of force parallel to the particular rotational axis without additional force deflection. In this way, a constructively simple solution results. In one embodiment, which requires no additional force deflection or rerouting, the brakes comprise lamellas having friction linings and entrainment means. The entrainment means of sequentially arranged lamellas alternately engage in the inner tube and the outer tube of the parts of the rotational joint, which can be rotated counter to each other. Here, it is possible to latch the various rotary joints even with different braking force in that the brakes of the various rotary joints have varying numbers of lamellas.

To generate the braking force, the braking pressure is applied to the brakes or the pins preferably by means of one or more pressure springs.

In an alternate embodiment of the brakes, rollers are provided between the inner tube and the outer tube of each rotary joint and the axes of the rollers extend parallel to the tube axis. The rollers are pressed against the inner tube by springs along a V-shaped surface on the outer tube. The pins have inclined surfaces in the region of the rollers for releasing the brakes. Because of these surfaces, the rollers are pressed toward the outside against the force of the pressure springs with the activation of the operator lever. Clamping-roller free-running brakes of this kind make possible extremely high holding forces and are free of play but lead also to high radial forces on the bearing locations of the rotary joints. Furthermore, the holding forces cannot be metered and a rotation of the rotary joint is virtually precluded when the brakes are latched and it is not easily possible to provide varying braking forces for the different rotary joints.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
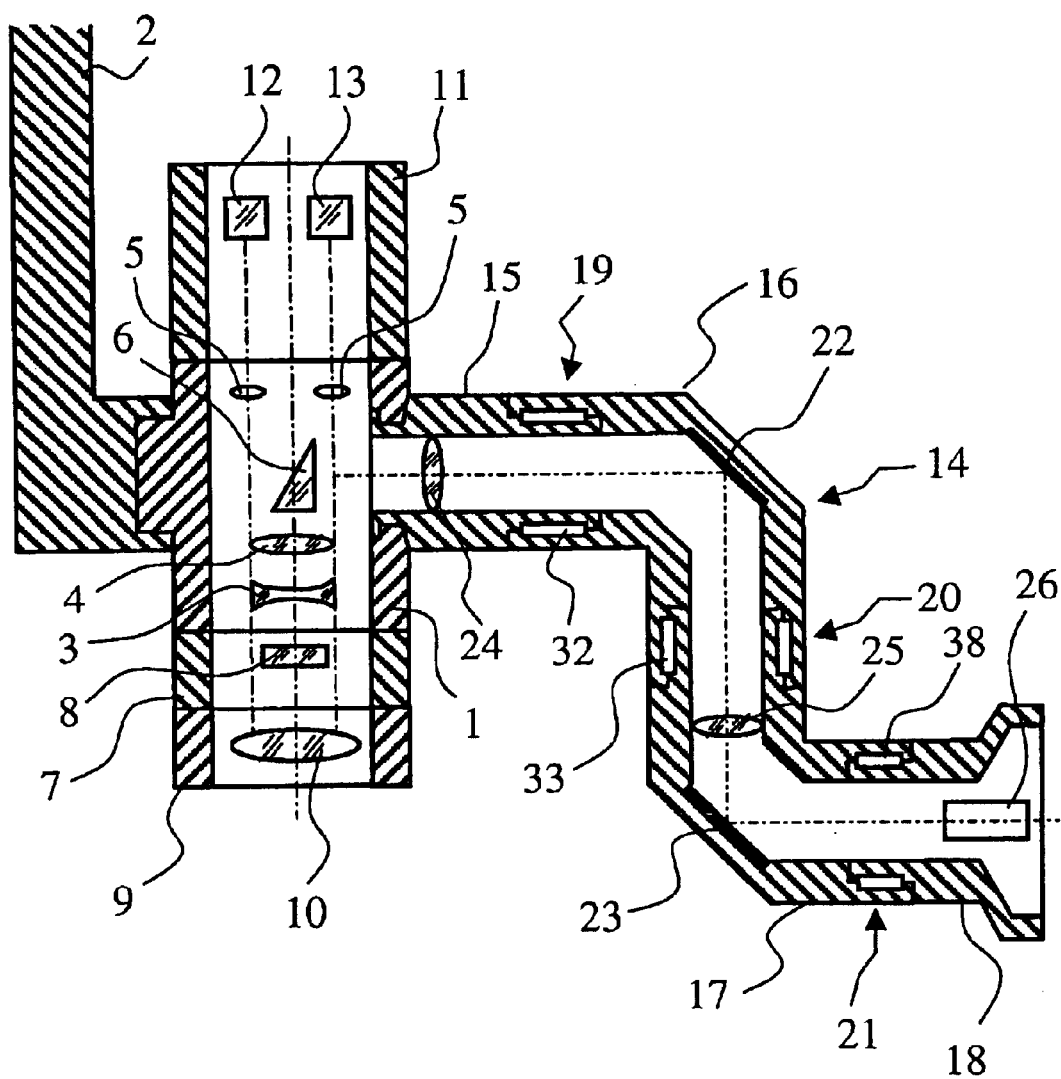
FIG. 1 shows a surgical microscope, in section, having a tube according to the invention and the section plane contains the optical axis.

The surgical microscope in FIG. 1 includes a microscope base body 1 with which the microscope is accommodated on a stand 2 not shown in greater detail. The microscope base body includes a magnification changer (3, 4) or a zoom system for changing the magnification. Furthermore, two deflecting prisms 6 are provided in the microscope base body or on a separate module accommodated on the base body. The viewing beam path is deflected in the direction toward the assistant viewer tube 14 with the aid of the two deflecting prisms 6.

An illuminating module 7 extends from the microscope base body therebelow and has an in-coupling optic for the illumination (not shown in greater detail) and in-coupling mirrors 8. The objective module 9 follows after the illuminating module 7 and has a main objective 10 accommodated therein. The ocular tube 11 for the main viewer is mounted above the microscope base body 1 and has the two tube lenses 5 for the two stereoscopic component beam paths (these component beam paths can extend partially into the microscope body) and separate deflecting prisms (12, 13). The actual microscope viewing location for the main viewer is not shown in FIG. 1 and would lie in a plane parallel to the plane of the drawing in FIG. 1.

The assistant viewer tube 14 is connected laterally on the microscope main body 1 or on a divider module accommodated thereon. The assistant viewer tube has an essentially z-shaped configuration and comprises four tube parts (15, 16, 17, 18) of which the two center tube parts (16, 17) are elbow pieces. The first tube part 15 is accommodated with one end on the microscope base body 1. The second tube part 16 is configured as the first elbow piece and, with one end, is received at the second end of the first tube part 15 rotatable about the tube axis of the tube part 15 so that a first rotary joint 19 is disposed between the second tube part 16 and the first tube part 15. The third tube part is configured as a second elbow piece 17. The third tube part is accommodated with one end on the second end of the second tube part 16 so as to be rotatable about the tube axis of the second tube part 16 so that a second rotary joint 20 is disposed between the second elbow part and the first elbow part. The tube axis of the second tube part 16 runs bent at an angle to the tube axis of the first tube part 15. The ocular support 18 extends at the other end of the third tube part 17. The ocular support 18 is, in turn, rotatable about the tube axis of the second angled tube part 17 so that a third rotary joint 21 is disposed between the fourth tube part and the third tube part. The first and third rotary joints (19, 21) then lie in mutually parallel planes spaced from each other, while the second rotary joint disposed therebetween permits a rotation about a plane perpendicular to the two other rotary joints. A rotation about the first rotary joint 19 serves for adjusting the viewing elevation in the assistant viewer tube and the rotation about the second rotary joint 20 serves to adjust the viewing direction in the assistant viewing tube 14 and the rotation about the third rotary joint 21 functions for adjusting the ocular view corresponding to the inclination of the head of the assistant viewer and/or that the optical axes of the two oculars 26 of the assistant viewer tube 14 lie in an essentially horizontal plane. A rotatability about 360° is possible about all three rotary joints (19, 20, 21).

In the interior clear space of the assistant viewer tube 14, the following are mounted: deflecting mirrors (22, 23) (in respective elbow pieces (16, 17)) and lens systems (24, 25), which conjointly define an afocal system having an intermediate image, and two prisms 26 for dividing the beam paths into the two oculars of the ocular tube (not shown) which is to be mounted for the assistant viewer.

Brakes (32, 33, 38) are provided in the rotary joints to avoid unwanted rotations about the rotary joints (19, 20, 21).

In the illustrated embodiment, the brakes (32, 33, 38) comprise floatingly journalled annular-shaped lamellas which are coated with friction linings. The respective outer lamellas as well as every second lamella following thereupon engages in the corresponding inner tube of the rotary joint via entrainment devices and each second remaining lamella engages via entrainment devices in the particular outer tube of the rotary joint. The engagement of the lamellas in the respective outer tube or inner tube of the rotary joint is virtually free of play in the azimuthal direction, that is, with respect to rotations about the corresponding tube axis; whereas, the lamellas are floatingly journalled in the direction of the respective tube axis and have play in this direction. When the brakes are latched, only a very small play is present in the rotary joints.

The two outermost lamellas of each lamella packet (which defines a corresponding brake) engage either both in the outer tube or both in the inner tube. The number of lamellas in each lamella package, which collectively defines a brake, is accordingly uneven. The number of lamellas in each of the three rotary joints (19, 20, 21) can be selected differently because the friction force of the brake is defined in the latched state via the number of lamellas. The first rotary joint 19 includes the largest number of lamellas 32 so that, for a latched brake, the rotation about this rotary joint 19 is held strongest because, at this rotary joint, the largest torques can occur. The number of lamellas of the lamella packets (33, 38), which follow in the direction toward the ocular viewing location, decreases in the direction toward the ocular view 26; that is, the braking action in the second rotary joint 20 is less than the braking action in the first rotary joint 19 and the braking action in the third rotary joint 21 is less than the braking action in the second rotary joint 20.

Figure 2:
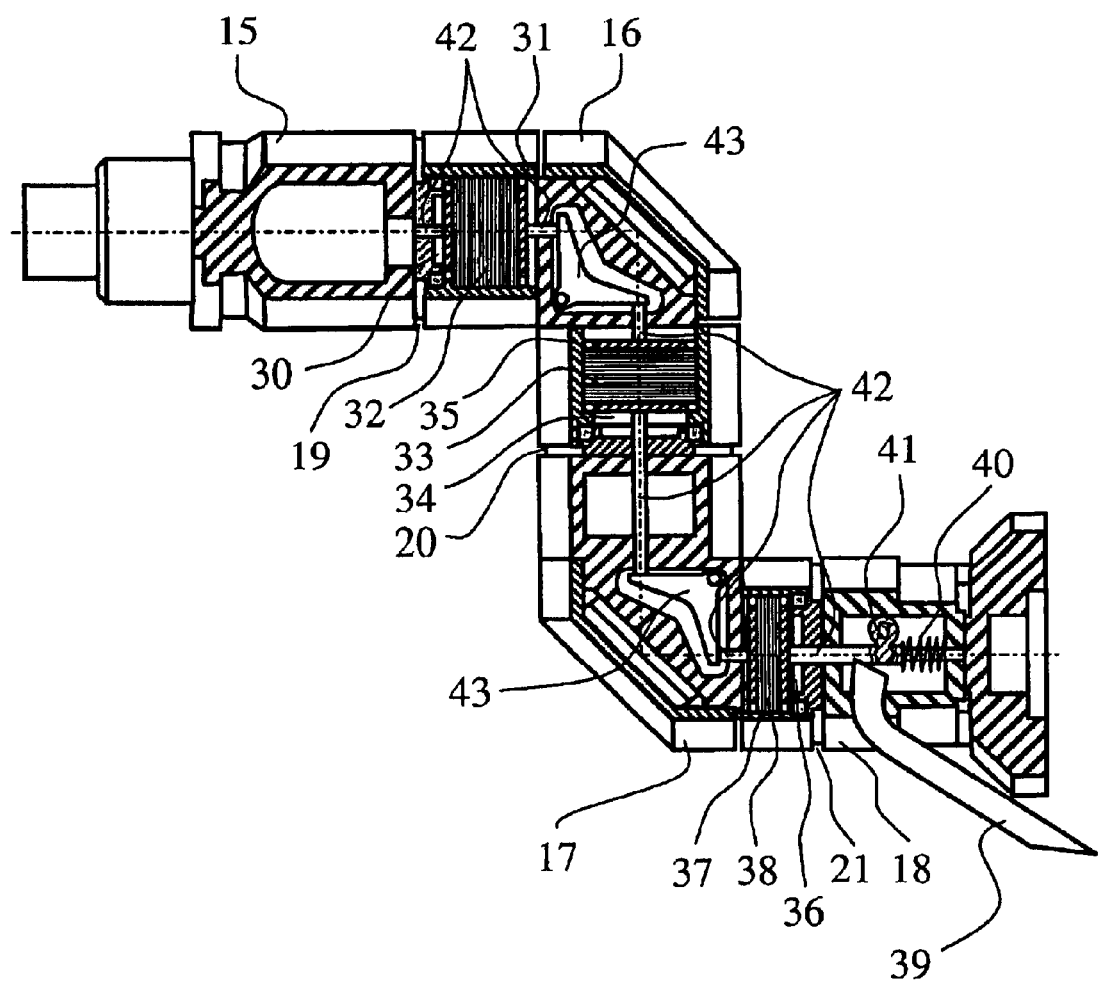
FIG. 2 shows a section through the assistant viewer tube in FIG. 1 in a section plane parallel to FIG. 1.

All three brakes (32, 33, 38) can be released by actuating a common operator lever 39 (FIG. 2). The operator lever 39 is mounted at the ocular end of the tube 14 on the fourth tube part 18 for ergonomic reasons. The mechanics for the transmission of an actuation of the operator lever 39 as well as for applying the brakes with the necessary braking force takes place via a system of pins and deflecting levers which are mounted in the tube wall of the tube 14 and are explained in greater detail with respect to FIG. 2.

As already mentioned above, each of the brakes (32, 33, 38) comprises a packet of annular-shaped lamellas, which alternately engage via entrainment devices in the inner tube (30, 34, 36) and in the outer tube (31, 35, 37) of the particular rotary joint. The lamella packets are delimited on both ends by respective annular discs, of which one is accommodated floatingly on the outer tube and the other floatingly on the inner tube of the rotary joint in each case. All three brakes are connected to each other via a system of pins 42 whose movement in the elbow pieces (16, 17) is deflected via pivot levers 43. To apply a force to all three brakes (32, 33, 38) with a unitary braking pressure, the system of pins and deflecting levers is pretensioned via a pressure spring 40 at one end. The pressure spring 40 presses on the ocular end of the system of pins 42 and pivot lever 43. The ocular-end pin presses on the brake 38 of the third rotary joint and presses the corresponding lamellas of the brake 38 together. The braking pressure, which is generated by the pressure spring 40, is transmitted to the second brake 33 and from there via two further pins and a pivot lever 43 to the microscope end brake 32 via the subsequent system of pins 42 and pivot levers 43. A further pin piece can be accommodated in the interior tube of the first tube section 15 and serves as a support. With a rotation about the rotary joints, the pins each glide over the surface of the annular disc accommodated floatingly on the inner tube of the rotary joint so that the transmission of the brake pressure via the pin-pivot-lever system is ensured in all rotation positions.

The operator lever 39 engages via an entrainment device 41 between the pressure spring 40 and the ocular-end third brake 38 in the system of pins 42 and pivot levers 43. With the actuation of the operator lever 39, the ocular end of the pin-pivot-lever system is moved against the force of the pressure spring 40 in the direction toward the ocular. In this way, the braking force, which is generated by the pressure spring 40, is withdrawn. All three brakes are simultaneously released because of the serial arrangement of the brakes (32, 33, 38).

Two systems of pins 42 and pivot levers 43 are provided in two mutually parallel planes lying at 180° offset to each other and referred to the tube axis so that the floatingly journalled lamellas of the brakes are not tilted.

The operator lever 39 is mounted on the ocular end last tube part which faces toward the operator and connects both pin-pivot-lever systems. The prisms for dividing the beam path into the two oculars are arranged in the same plane as the engagements of the operator lever in the pin-pivot-lever system in the last tube part. In this way, the operator lever remains arranged the same referred to the orientation of the ocular tube even for a rotation about the rotary joints.

Figure 4:
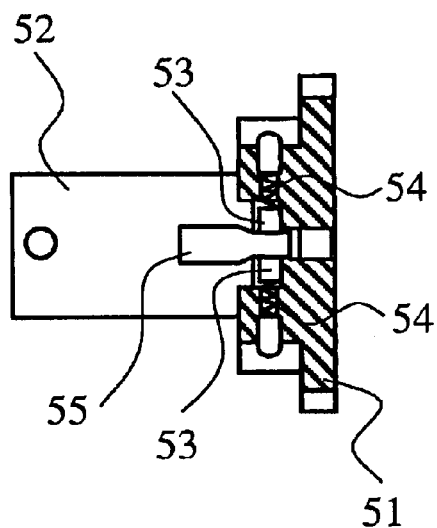
Figure 3:
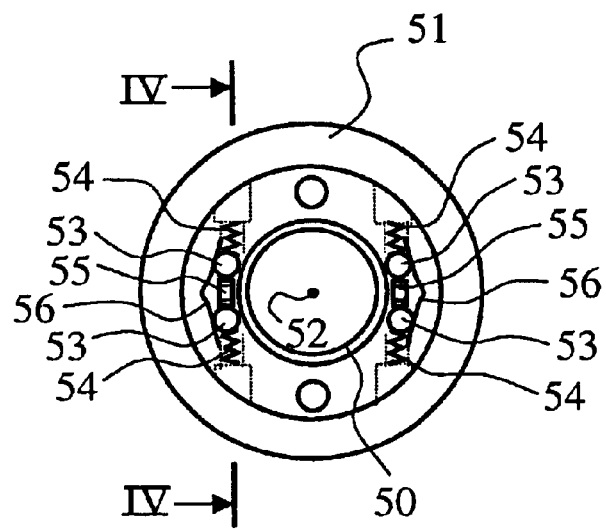
FIG. 3 shows a section view perpendicular to the tube axis of an alternate embodiment of the invention; and, FIG. 4 shows the section through the embodiment in FIG. 3 in a section plane perpendicular to FIG. 3.

In FIGS. 3 and 4, an alternate embodiment for the brakes in the rotary joints is shown. Here, the brakes are the so-called clamp-roller free-running brakes. For this type of brakes, the outer tube 51 of the rotary joint comprises approximately V-shaped inner surfaces 56 in which the rollers 53 are seated with their axes parallel to the rotational axis 52 of the rotary joint. Furthermore, the brakes include springs 54 via which the rollers 53 are subjected to a pressure force perpendicular to the roller axes. With the pressure force of the springs 54, the rollers 53 are pressed along the V-shaped surfaces 56 of the inner tube 51 and so clamp the rotary joint tight. The actuating rods 55 are arranged between the rollers 53 and have axes which likewise extend parallel to the rotational axis 52 of the rotary joint and, in the region of the rollers 53, have inclined surfaces facing toward the rollers 53. When the actuating rods 55 are actuated, they press the rollers 53 apart whereby the brake of the rotary joint is released. The brakes, which belong to the several rotary joints connected in series one behind the other, can also be coupled in series with each other in this embodiment in that the actuating rods 55 are configured as a system of pins and pivot levers, which connect the brakes to each other belonging to the rotary joints connected one behind the other or can be actuated via a corresponding system of pins and pivot levers. In contrast to the embodiment of the brakes via annular-shaped lamellas described with respect to FIGS. 1 and 2, the holding force of the brake, however, cannot be metered in such clamp-roller free-running brakes; that is, all rotary joints have the same stiffness when the brakes are latched and an intended rotation in the rotary joint is not possible when the brakes are applied or leads to possible damage at the mutually clamping surfaces.

An embodiment according to the invention with a clamp-roller free-running brake has, aside from the different configuration of the brakes, otherwise a configuration analog to the embodiment shown in FIGS. 1 and 2 so that reference to the above description of the figures is made.

It is understood that the foregoing description is that of the preferred embodiments of the invention and that various changes and modifications may be made thereto without departing from the spirit and scope of the invention as defined in the appended claims.

What is claimed is:

1. A tube assembly for an optical instrument, the tube assembly comprising:

a first rotary joint;

a first brake for latching said first rotary joint;

a second rotary joint;

a second brake for latching said second rotary joint;

an operator-controlled device operatively connected to said first and second brakes;

said operator-controlled device being switchable between a first state wherein said first and second brakes are applied to said rotary joints and a second state wherein said first and second brakes are released to permit movement of said rotary joints; and, said operator-controlled device further including a system of pins and pivot levers for transmitting a movement of said operator-controlled element to said first and second brakes.

2. The tube assembly of claim 1, further comprising a plurality of tube parts interconnected by said rotary joints including a first tube part facing toward the operator; and, said operator-controlled device including an operator-controlled element mounted in said first tube part and being actuable by an operator to bring said operator-controlled device into said second state.

3. The tube assembly of claim 1, wherein said first and second brakes each include at least one pressure spring for applying a braking force to the brake when said operator-controlled device is in said first state.

4. The tube assembly of claim 1, wherein each of said rotary joints defines a rotation axis; and, each of said brakes being releasable in response to a force applied parallel to the rotation axis without further force deflection.

5. The tube assembly of claim 4, wherein said pressure springs act on said system of pins and pivot levers; and, said operator-controlled element acts upon said system.

6. The tube assembly of claim 1, each of said rotary joints including an inner tube part and an outer tube part; and, each of said brakes including an arrangement of lamellas having friction linings and an entrainment device for alternately engaging said inner tube part and said outer tube part.

7. The tube assembly of claim 6, wherein said first brake and said second brake include different numbers of lamellas.

8. The tube assembly of claim 1, each of said rotary joints including an inner tube part and an outer tube part; said inner tube part and said outer tube part defining a tube axis; each of said brakes including an arrangement of rollers extending parallel to said tube axis in the region of said rotary joints; and, an arrangement of springs for pressing the rollers against the inner tube.

9. The tube assembly of claim 1, further comprising a third rotary joint which is defining a rotating axis arranged perpendicular to an axis of rotation defined by the first rotary joint and the second rotary joint.

10. The tube assembly of claim 1, further comprising optical elements arranged in the interior of said tube arrangement for transmitting an optical beam path.

11. The tube assembly of claim 1, wherein said system of pins and pivot levers is arranged in a wall of said tube assembly.

12. The tube assembly of claim 2, further comprising a prism pair arranged in said first tube part facing toward the operator for dividing a beam path into the oculars of an ocular tube which is mounted or is to be mounted.

13. A tube assembly for an optical instrument, the tube assembly comprising:
- a first rotary joint;
- a first brake for latching said first rotary joint;
- a second rotary joint;
- a second brake for latching said second rotary joint;
- an operator-controlled device operatively connected to said first and second brakes;
- said operator-controlled device being switchable between a first state wherein said first and second brakes are applied to said rotary joints and a second state wherein said first and second brakes are released to permit movement of said rotary joints;
- a plurality of tube parts interconnected by said rotary joints including a first tube part facing toward the operator; and,
- said operator-controlled device including an operator-controlled element mounted in said first tube part and being actuable by an operator to bring said operator-controlled device into said second state.

14. A tube assembly for an optical instrument, the tube assembly comprising:
- a first rotary joint;
- a first brake for latching said first rotary joint;
- a second rotary joint;
- a second brake for latching said second rotary joint;
- an operator-controlled device operatively connected to said first and second brakes;
- said operator-controlled device being switchable between a first state wherein said first and second brakes are applied to said rotary joints and a second state wherein said first and second brakes are released to permit movement of said rotary joints;
- each of said rotary joints including an inner tube part and an outer tube part; and,
- each of said brakes including an arrangement of lamellas having friction linings and an entrainment device for alternately engaging said inner tube part and said outer tube part.

15. A tube assembly for an optical instrument, the tube assembly comprising:
- a first rotary joint;
- a first brake for latching said first rotary joint;
- a second rotary joint;
- a second brake for latching said second rotary joint;
- an operator-controlled device operatively connected to said first and second brakes;
- said operator-controlled device being switchable between a first state wherein said first and second brakes are applied to said rotary joints and a second state wherein said first and second brakes are released to permit movement of said rotary joints;
- each of said rotary joints including an inner tube part and an outer tube part;
- said inner tube part and said outer tube part defining a tube axis;
- each of said brakes including an arrangement of rollers extending parallel to said tube axis in the region of said rotary joints; and,
- an arrangement of springs for pressing the rollers against the inner tube.

16. A tube assembly for an optical instrument, the tube assembly comprising:
- a first rotary joint;
- a first brake for latching said first rotary joint;
- a second rotary joint;
- a second brake for latching said second rotary joint;
- an operator-controlled device operatively connected to said first and second brakes;
- said operator-controlled device being switchable between a first state wherein said first and second brakes are applied to said rotary joints and a second state wherein said first and second brakes are released to permit movement of said rotary joints; and,
- optical elements arranged in the interior of said tube arrangement for transmitting an optical beam path.

17. The tube assembly of claim 13, further comprising a prism pair arranged in said first tube part facing toward the operator for dividing a beam path into the oculars of an ocular tube which is mounted or is to be mounted.

18. A tube assembly for an optical instrument, the tube assembly comprising:
- a first rotary joint;
- a first electromagnetic brake for latching said first rotary joint;
- a second rotary joint;
- a second electromagnetic brake for latching said second rotary joint;
- an operator-controlled device operatively connected to said first and second electromagnetic brakes; and,
- said operator-controlled device being switchable between a first state wherein said first and second electromagnetic brakes are applied to said rotary joints and a second state wherein said first and second electromagnetic brakes are released to permit movement of said rotary joints.

* * * * *